(12) United States Patent
Villada et al.

(10) Patent No.: US 11,839,491 B2
(45) Date of Patent: Dec. 12, 2023

(54) SHAPE-MEMORY IN-EAR BIOSENSOR FOR MONITORING PHYSIOLOGICAL SIGNALS

(71) Applicant: The Regents of the University of Colorado, a body corporate, Denver, CO (US)

(72) Inventors: Andres Villada, Boulder, CO (US); Dana Stamo, Boulder, CO (US); Zhanan Zou, Boulder, CO (US); Jianliang Xiao, Louisville, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 499 days.

(21) Appl. No.: 17/064,723

(22) Filed: Oct. 7, 2020

(65) Prior Publication Data

US 2021/0100509 A1 Apr. 8, 2021

Related U.S. Application Data

(60) Provisional application No. 62/911,826, filed on Oct. 7, 2019.

(51) Int. Cl.
*A61B 5/00* (2006.01)
*A61B 5/24* (2021.01)

(52) U.S. Cl.
CPC .......... *A61B 5/6817* (2013.01); *A61B 5/0006* (2013.01); *A61B 5/24* (2021.01); *A61B 2562/125* (2013.01); *A61B 2562/16* (2013.01); *A61B 2562/227* (2013.01)

(58) Field of Classification Search
CPC ....... A61B 5/6817; A61B 5/0006; A61B 5/24; A61B 2562/125; A61B 2562/16; A61B 2562/227; A61B 5/4806; A61B 5/291; A61B 5/296; A61B 5/297; A61B 5/4094; A61B 5/263; A61F 11/10
See application file for complete search history.

(56) References Cited

U.S. PATENT DOCUMENTS

| 8,307,942 | B2 * | 11/2012 | Benner | A61F 11/08 181/135 |
| 2002/0025055 | A1 * | 2/2002 | Stonikas | H04R 25/658 381/328 |
| 2008/0249389 | A1 * | 10/2008 | Haug | A61B 5/282 600/372 |
| 2017/0281416 | A1 * | 10/2017 | O'Leary | A61F 11/14 |

(Continued)

*Primary Examiner* — Eric F Winakur
*Assistant Examiner* — Emily C Clement

(57) ABSTRACT

Systems and methods for a shape-memory in-ear biosensor for polysomnography and monitoring physiological signals are provided. Various embodiments include an earpiece made from a shape memory or temperature-dependent phase transition material embedded into polydimethylsiloxane elastomer body. The earpiece can use electrodes to detect physiological signals by making direct contact with a user's skin and without the use of electrically conductive gel. When heated above the glass transition temperature of the shape memory polymer, various embodiments of the biosensor may be folded. When cooled, the biosensor will maintain the folded shape. The folded biosensor may then be inserted into the ear canal of a user where, in response to heating by the user's body, it partially unfolds to conform to the shape of the ear canal.

17 Claims, 11 Drawing Sheets

(56) References Cited

U.S. PATENT DOCUMENTS

| | | | | |
|---|---|---|---|---|
| 2018/0177421 A1* | 6/2018 | Kilsgaard | .............. | A61B 5/725 |
| 2018/0206788 A1* | 7/2018 | Andersen | .............. | A61B 5/6867 |
| 2020/0027568 A1* | 1/2020 | Foshee, Jr. | ............... | A61B 7/02 |
| 2020/0077192 A1* | 3/2020 | Prevoir | .............. | C08G 18/7671 |
| 2020/0374615 A1* | 11/2020 | Anderson | .............. | G16H 80/00 |

* cited by examiner

SHAPE-MEMORY IN-EAR BIOSENSOR FOR MONITORING PHYSIOLOGICAL SIGNALS

CROSS-REFERENCE TO RELATED APPLICATIONS

This application claims priority to U.S. Provisional Patent Application No. 62/911,826 filed Oct. 7, 2019, which is incorporated herein by reference in its entirety for all purposes.

TECHNICAL FIELD

Various embodiments of the present technology generally relate to biosensors. More specifically, some embodiments of the present technology relate to a shape-memory in-ear biosensor for polysomnography (PSG) and other physiological signals.

BACKGROUND

Medical researchers have demonstrated that sleep at night deeply impacts health and behavior as well as the efficiency of work or school performance in the long term. In the past, accurately evaluating sleep quality required an identification of sleep stages through an assessment of bioelectrical signal patterns generated by brain activities, eye movements, and muscle contraction. In order to capture these signals, overnight polysomnography (PSG) studies are performed to record typical electroencephalography (EEG), electrooculography (EOG), and electromyography (EMG). However, such conventional recordings using polysomnography (PSG) incur drawbacks including: the large number of wired sensors attached to the human body, the need for a messy conductive gel, which decreases in performance over time, the need of professional installation and periodic checkup in a sleep laboratory, the risk of lead failure as patients drop them with movements, and the high cost of the system itself.

As such, there are a number of challenges and inefficiencies created in traditional PSG devices. For example, traditional polysomnography devices are unable to function without numerous electrodes arranged at specific reference points on the head of a patient. Furthermore, these devices must utilize electrically conductive gel to function properly. Thus, it can be difficult to perform polysomnography in a comfortable and effective manner and further serves to limit polysomnography to a laboratory setting. It is with respect to these and other problems that embodiments of the present invention have been made.

SUMMARY

Various embodiments described herein relate to systems, methods of use, and methods for manufacturing an in-ear biosensor for the detection of the brainwaves of a user. In some embodiments, a system includes an earpiece made from a shape memory polymer (SMP) fully encapsulated inside of an elastomer. A plurality of convex bumps or surface features may exist on the outer surface of the elastomer. The system may further contain a set of electrodes adhered to the surface of the earpiece. The set of electrodes can be adhered to a set of the plurality of convex bumps through the use of a double-sided adhesive. A set of wires can be adhered to the set of electrodes by an electrically conductive epoxy and an insulating heat shrink. An additional layer of elastomer may be overlaid onto the set of flexible conductive electrodes such that the electrodes are partially covered. The set of flexible conductive electrodes includes electrodes with copper, gold, silver, platinum, titanium, graphite, graphene, nanotubes, nanowires, polymers, nanoparticles, polymer composites, microparticle composites, nanoparticle composites, or combinations thereof.

The shape memory polymer that is encapsulated in the earpiece can be configured to have a programmed state and a fixed state and may transition from the programmed state to the fixed state when the temperature of the shape memory polymer is raised above the glass transition, or phase transition, temperature of the shape memory polymer. Human body temperatures range from 36.1 degrees Celsius (° C.) to 37.2° C. In some embodiments, the glass transition, or phase transition, temperature can fall in a range greater than room temperature and slightly above normal human body temperature (e.g., between 70-105 degrees Fahrenheit (° F.), where "room temperature" is defined as 15° C. to 25° C. More specifically, the phrase "slightly above a body temperature of a user" means that the range of glass transition, or phase transition, temperatures may be up to 42° C. As such, in an embodiment, the aforementioned range of glass (or phase) transition temperatures can be from 20° C. to 50° C., or from 20° C. to 48° C., or from 30° C. to 50° C. In another embodiment, the range of glass (or phase) transition temperatures can be from 35° C. to 4° C. When the earpiece is heated above the glass (or phase) transition temperature of the shape memory polymer, the earpiece may be folded into a programmed state where the programmed state is a hollow cylindrical shape. The earpiece may be held in the programmed state by a mold and cooled to below the glass (or phase) transition temperature of the shape memory polymer. When this occurs, the earpiece can maintain the hollow cylindrical shape. Provided the range of normal human temperatures, the earpiece may expand more slowly in the ear of a user having a statistically lower body temperature. However, the 30° C. to 50° C. (or 30° C. to 50° C., or 35° C. to 42° C.) range of glass (or phase) transition temperatures according to the present technology can account for this normal variability in human body temperatures.

When the earpiece is folded into the programmed state, it may be inserted into an ear canal of a user. Once inserted into the ear canal of a user, the earpiece is heated above the glass (or phase) transition temperature of the shape memory polymer by the ear canal of the user. The earpiece then partially unfolds to conform with the shape of the ear canal of the user where a low impedance electrical connection is created between the set of flexible conductive electrodes and the surface of the ear canal without the use of electrically conductive gel. Furthermore, the set of flexible conductive electrodes are further positioned near the neutral mechanical plane of the earpiece. The set of flexible conductive electrodes may be cleaned by a salt and vinegar solution and are made from ultra-thin, silver electroplated copper, wherein "ultra-thin" means a thickness of the silver electroplated copper of from about (e.g., ±10% or less around the stated value) 5 microns to about 0.5 millimeters. In an embodiment, the thickness of the silver electroplated copper is about 25 microns. In other embodiments, about 5 microns is a minimum, and about 1 millimeter is a maximum, for the thickness of the silver electroplated copper. This can be due to copper film being less than about 5 microns breaking when rolled to the extent necessary for application in the present technology. This can also be due to copper film being greater than about 1 millimeter not being capable of adhering to the surface when rolled along with the earpiece according to the present technology. The electrically conductive epoxy can be made from an epoxy containing silver in some embodiments. The elastomer of the earpiece can be made from polydimethylsiloxane and the set of wires are a set of medical grade silver wires.

In other embodiments, a method for manufacturing a biosensor to facilitate the detection of brainwaves involves first applying a layer of oil to the inside of a biosensor shaped mold. A first layer of elastomer can then be poured into the mold and cured. Once the first elastomer layer is sufficiently cured, a shape memory polymer can be inserted into the mold onto the surface of the elastomer. A second elastomer layer can then be poured into the mold overtop of the shape memory polymer in such a way that the second elastomer layer fully encapsulates the shape memory polymer. The second elastomer layer can then be cured and once sufficiently cured, is removed from the mold and trimmed to desired shape of the biosensor.

In some embodiments, a sheet of copper can be cleaned. This can involve deoxidizing the surface of the copper sheet. The copper sheet can then be electroplated with an electrolyte solution. After the electroplating is finished, the electroplated copper sheet can be adhered to a double-sided adhesive and mechanically cut into a set of electrodes. The set of electrodes can then be adhered to the surface of the elastomer with the exposed surface of the double-sided adhesive. Once adhered, the electrodes are attached to a set of silver wires with an electrically conductive epoxy and then the epoxy is subsequently cured. A third elastomer layer can then be poured to partially cover the electrodes and the third elastomer layer is then cured.

The first, second, and third elastomer layers can be made from polydimethylsiloxane in various embodiments. The curing of each of these layers may involve heat treating the layers until they have solidified. When the first elastomer layer is poured into the biosensor shaped mold, a set of convex reliefs can be molded onto one side of the first elastomer layer. In some embodiments, the set of electrodes can be adhered to the convex reliefs of the first elastomer layer by using the double-sided adhesive. In still other embodiments, the electroplating of the copper sheet may include electroplating the copper sheet with a silver solution to form silver electroplated copper. Additionally, when attaching the set of electrodes to the set of silver wires, a heat shrink is used to bind the electrodes and the silver wires to the biosensor.

Some embodiments may have a relatively low electrode-skin contact impedance values without the need for conductive gels in the ear canal. For example, in some embodiments, the impedance may be as low as 10 kΩ, compared to over 100 kΩ for the majority of traditional system. The relatively lower impedance values are desirable because there will be less "noise" to drown out the biosignals. Various embodiments can achieve the relatively low impedance with the combination of the polymers and a unique shape that allows the earpiece to unroll inside of the outer ear canal at body temperature—instead of just expanding— as well as the flexibility and conductivity of the silver-electroplated electrodes. As such, the SMP backbone allows various embodiments of the biosensor to conform to a much greater variety of canal shapes and sizes without compromising the wearer's ability to hear.

While multiple embodiments are disclosed, still other embodiments of the present technology will become apparent to those skilled in the art from the following detailed description, which shows and describes illustrative embodiments of the technology. As will be realized, the invention is capable of modifications in various aspects, all without departing from the scope of the present technology. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings.

Figure 1:
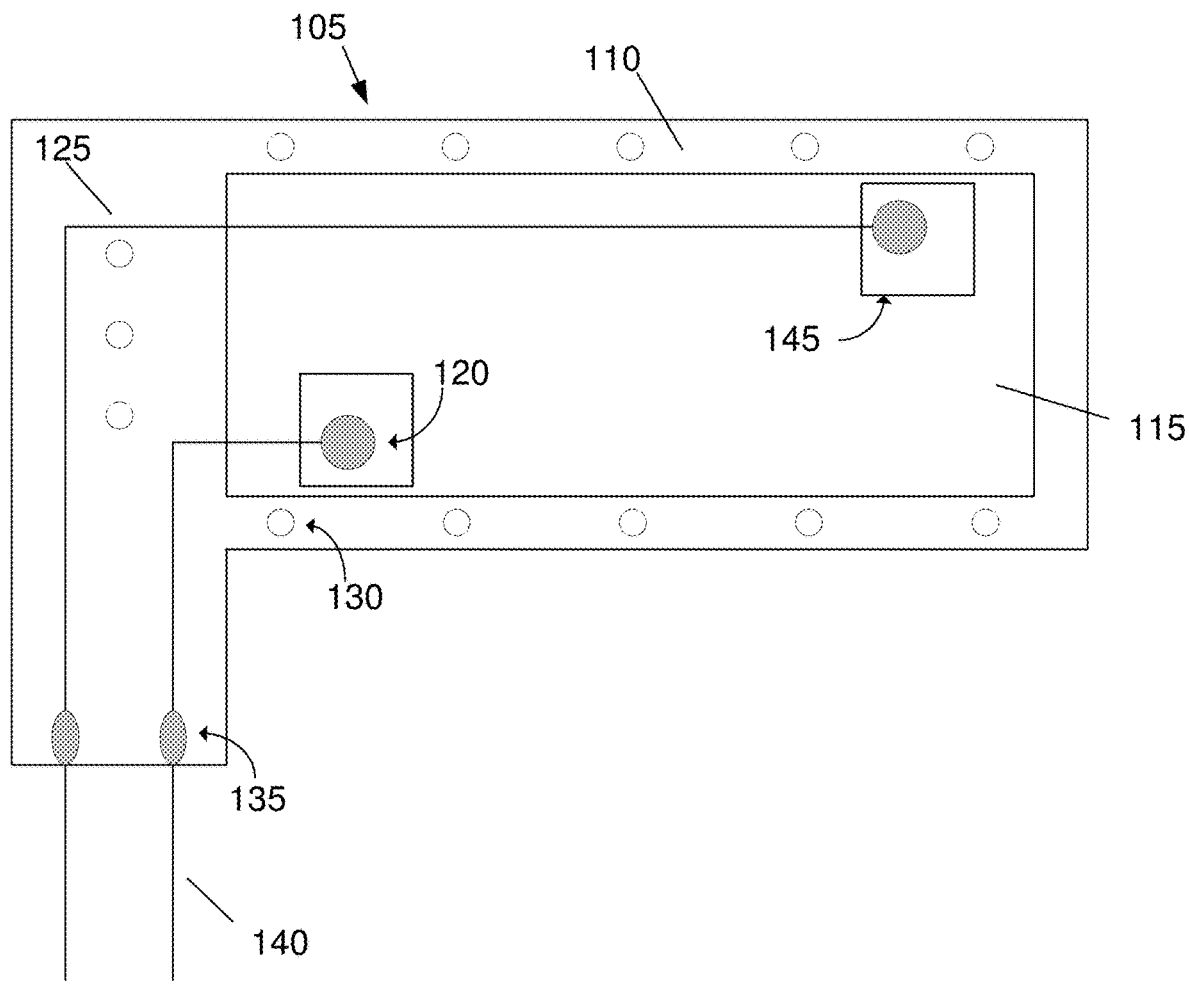
FIG. 1 illustrates an example of an in-ear biosensor in which some embodiments of the present technology may be utilized.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to biosensors associated with polysomnography. More specifically, some embodiments of the present technology relate to in-ear biosensors comprising shape-memory polymers coated in polydimethylsiloxane for use in detecting electroencephalography signals, electrooculography signals, and electromyography signals. Presently, the most conventionally reliable process of determining sleep stages is to record EEG, EOG, and EMG signals using the PSG system and then score them for clinical diagnoses. To date, nocturnal PSG remains the "gold standard" method for diagnosing sleep disorders. High cost and limited access to laboratory based PSG, however, can cause financial and travel burdens on patients and families, as well as delays in the diagnosis and treatment of sleep disorders. Additionally, environmental differences between laboratory polysomnograms and the average household may reduce the applicability of laboratory findings to the home setting or for people with developmental delays. Due to the need for a professional's application of the many wired sensors to the face and head, as well as the frequent need for manual scoring of bioelectrical signals, the PSG system has inherent disadvantages, such as high cost, time consumption, cumbersomeness, and human discomfort.

In contrast various embodiments of the present technology provide for a biosensors based on a shape-memory polymers (SMPs). As used herein, an SMP is a material having properties (e.g., stiffness) that change in response to an external stimulus (e.g., heating or cooling). In one embodiment, the SMP used in embodiments of the present technology experience a change in elastic modulus within a range of temperatures of from 30° C. to 50° C. On such SMP used in an example embodiment is a 4:1 ratio of tert-butyl acrylate and polyethylene glycol dimethacrylate using 2,2-Dimethocy-2-phenylacetophenone as a photoinitiator to bind the copolymers into a network. Similar behavior in the earpiece according to the present technology may be accomplished through a variety of temperature-dependent transitions with other materials. In another example, the SMP used in some embodiments takes advantage of the phase transition of metallic Gallium/Indium from solid to liquid, the temperature of which can be tuned depending on the ratio at which they are mixed. Numerous other SMPs may be suitable for use in the earpiece according to the present technology including, without limitation, various polymers, shape memory alloys (SMAa) and ceramics. In some embodiments, the SMP(s) used in the earpiece according to the present technology may be selected from a group including those SMPs that are known, or can be determined, to be biocompatible, such that upon contact of the earpiece with human skin, undesirable effects like irritation does not occur. The SMPs provide an excellent alternative to overcome many of the difficulties which are inherent to traditional PSG methods. SMPs have a wide range of potential applications which includes using them as a component in a shape-adaptive earpiece that allows for the collection of electrical bio-signal data from the surface of the ear canal. Although many polymers are known to exhibit some degree of shape change due to environmental stimuli, SMPs are remarkable for their ability to controllably recover large deformations from a programmed state to a fixed state. Although most polymers exhibit some degree of the Shape Memory Effect (SME) due to environmental stimuli, SMPs, as a class of polymers, are remarkable in their ability to recover large shape changes: up to 400% strain recovery, in some cases.

While the stimulus for the shape-memory effect may be light, humidity, or a magnetic field, the shape memory effect of the SMP is intrinsically related to its thermomechanics, as the functional effect of the external field is to raise the material temperature of the SMP above its glass transition temperature ($T_g$), or phase transition temperature. Below $T_g$, an amorphous SMP is in a reduced-free volume glassy state that restricts micro-Brownian motion but still exhibits non-equilibrium chain motion over extended time scales. Raising the temperature of the material above $T_g$ allows the chains to move (and be deformed) more freely as a series of relaxation processes take place. In one example, the $T_g$ of an example SMP according to the present technology is about 35° C., such that the example SMP remains in the glassy state below about 35° C. An insightful choice of crosslinking density allows for tuning of a material's shape-memory properties. As a class of smart materials, SMPs can memorize a very impressive variety of different shapes. A strain can be fixed in the deformed, temporary shape of SMP, even after the force is removed. When appropriate stimulus is applied, the SMP can recover to its original, permanent shape. Depending on the materials, different stimuli can be used to trigger the recovery behavior, including temperature, light, humidity, electric and magnetic field.

To overcome the deficiencies of traditional PSG devices, some embodiments provide for a biosensor designed with two pairs of passive electrodes (e.g., electroplated with gold or silver chloride) embedded on a soft polymer (PDMS) earpiece is presented. The trade name for the PDMS elastomer is Sylgard 184, but various embodiment of the earpiece can be manufactured out of any elastomer with an elastic modulus between approximately 50 kPa and 10 MPa. In some embodiments, the earpiece can be designed to be shaped like a regular earbud or earplug with electrodes on the surface and an SMP inside to endow it with the shape memory effect that would make it function essentially the same way once inside the ear, but it would have to be pinched (e.g., similar to foam ear plugs) to get it in the ear canal. This design can easily include a canal through the middle of the earpiece to allow sound to travel through.

To measure the bioelectrical signal inside the ear, this biosensor is rolled and inserted into the subject's right and left ear canals. The polymer earpiece was selected as a sensory receiver because it is soft and easily placed inside the ear, expanding once inside to maximize the electrode contact with the ear canal. It is fitted with a SMP that can maintain a small rolled shape underneath body temperature, but slowly unfurls to fit the intricate structure of the individual's ear canal as it is heated by the body. In accordance with various embodiments, the SMP can be an amorphous tert-butyl acrylate network. However, the process for manufacturing and using the earpiece would be the same for essentially any material with a transition temperature around body temperature.

In accordance with various embodiments, the earpiece can ensure a firm and constant electrical connection between the electrodes and the skin while guaranteeing mobility for the increased length of time that would be required during a sleep episode. All of the polymer materials used to make the earpiece are biocompatible in their cured form and pose no health risks inside the ear canal. The passive electrodes can be made from ultra-thin silver-electroplated copper and designed to run along the central mechanical plane of the earpiece for maximum comfort, low contact impedance, and long term robustness. Each electrode can be implanted in the polymer earpiece and adhered to convex bumps on its surface for optimal skin/electrode contact with the ear canal. The soft polymer bumps also ensure the comfort of the user while pressure is applied to the electrodes.

At the base of the earpiece, the electrodes can be connected to silver wires using silver epoxy for the minimum possible impedance. The wires can connect the biosensor to a wireless transmission module or logic board (e.g., an OpenBCI Board) and are well-insulated and of a length similar to that of normal in-ear headphones to ensure a safe distance between the board and the user's face. In accordance with various embodiments, the device can deliver no energy to its users; these electrodes are purely for detection purposes, similar to the electrodes that users are exposed to for a normal polysomnogram. With this design, the bioelectrical signal collecting system simply acts as a receiver and translator of physiological data measured inside the ears during a sleep episode without delivery of any energy, transmissions, or electrical signals to the subject.

Some embodiments relate to a biosensor that can be positioned inside the ear canal of a user to capture brainwaves of the user. The in-ear biosensor can include a fully encapsulated SMP that serves as a backbone to the biosensor. The fully encapsulated SMP can have a glass (or phase) transition temperature near body temperature and above that of room temperature. The SMP may have a fixed state and a programmable state. When heated above the glass (or phase) transition temperature, the SMP may be folded into specific shape which constitutes a programmed state and continues to hold this programmed state when cooled below its glass (or phase) transition temperature. When the SMP is in a programmed state and is heated above the glass (or phase) transition temperature, the SMP can unfold and return to the fixed state.

In other embodiments, the biosensor can contain electrodes that are positioned on the outer surface of the biosensor that can capture the brainwaves of a user when pressed against the skin of the ear canal of a user. The set of electrodes may capture the brainwaves of a user through contact with the surface of the ear canal and without the use of any electrically conductive gels. The set of electrodes may be adhered to the surface of the biosensor by a double-sided adhesive. Additionally, the electrodes may be electroplated by a different type of metal to increase their electrical conductivity while maintaining their original structural properties. The set of electrodes may be attached to external wires by an electrically conductive epoxy and electrically conductive epoxy may include the same metal used to electroplate the electrodes. Furthermore, the electrically conductive wires also include the same metal used to electroplate the electrodes.

In some embodiments, the body of the biosensor may be made from a flexible, non-toxic elastomer. The elastomer may be molded into the shape of the biosensor and fully encapsulate the SMP. The elastomer may contain convex surface features where the electrodes can be mounted and may cover the non-sensing sections of the electrodes while leaving the sensing-sections of the electrodes exposed. The elastomer my further conform to the shape of the SMP when SMP transitions from a programmed state to a fixed state or when the SMP transitions from a fixed state to a programmed state.

In accordance with various embodiments, the biosensor may be heated and then folded into a hollow cylindrical shape using a mold. The biosensor may then cool and retain the hollow cylindrical shape. After the biosensor has cooled, it can be inserted into the ear canal of the user. Once inserted into the ear canal of a user, the biosensor will heat up due to the body temperature of the user which causes the SMP embedded in the biosensor to transition from the programmed state to the fixed state. This causes the biosensor to partially unfurl thereby conforming to the structure of the ear canal of the user. After the biosensor has conformed to the shape of the ear canal of the user, the biosensor may record brain waves with low impedance. The biosensor may detect a variety of different physiological signals and/or environmental signals. For example, some embodiments can detect one or more of the following: electroencephalography (EEG) signals, electrooculography (EOG) signals, electromyography (EMG) signals, temperature, heart rate, blood pressure, accelerations, electrocardiogram (EKG or ECG), and/or the like.

Various embodiments of the present technology provide for a wide range of technical effects, advantages, and/or improvements to biosensors and components. For example, various embodiments include one or more of the following technical effects, advantages, and/or improvements: 1) a low-cost, flexible, and comfortable device that employs low-impedance electrodes on a shape-adaptive polymer earbud; 2) efficient detection of low-voltage EEG, EMG, and EOG signals via direct-to-skin contact by conforming to the contours of the ear canal; 3) integrated use of shape memory polymers and elastomers to create a custom fitting biosensor; 4) use of unconventional and non-routine materials and operations to a high signal to noise ratio without the need for a conductive gel inside the ear; and/or 5) cross-platform integration of biosensors with machine learning to more efficient identification of automatic health monitoring and classifications (e.g., sleep stage classification or other diagnostics).

In the following description, for the purposes of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to in-ear biosensor devices embodiments of the present technology are equally applicable to various other form factors and sensing applications. For example, some embodiments of the biosensor can also be used to detect biosignals throughout the body by making firm contact between the electrodes and the skin. It could, for example, be held against the chest and detect heart rhythms.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

FIG. 1 illustrates an exemplary biosensor 105 in which some of the embodiments of the present technology may be utilized. In the embodiments illustrated in FIG. 1, biosensor 105 includes elastomer body 110, shape memory polymer 115, electrode heads 120, electrode tails 125, convex bumps 130, conductive epoxy 135, external wires 140, and/or double sided adhesive 145. Other embodiments may include other features or components or selective combinations of the components shown in FIG. 1.

FIG. 1 shows a top-down view of biosensor 105 and includes elastomer body 110. Elastomer body 110 can form the superstructure of the earpiece and fully encapsulates shape memory polymer 115, as well as electrode tails 125 and electrically conductive epoxy 135. In accordance with various embodiments, elastomer body 110 may be made from polydimethylsiloxane or any other soft, non-toxic polymer. Some embodiments may include convex bumps 130 on the surface of elastomer body 110. Convex bumps 130 can be made from the same elastomer as elastomer body 110 and are formed during the molding process. Convex bumps 130 can serve to maintain comfort and pressure whilst in a user's ear canal and further force biosensor 105 to fold in a specific way. When biosensor 105 is folded into a hollow cylindrical shape, convex bumps 130 can partially lock the biosensor into shape.

Encased in elastomer body 110 is shape memory polymer 115. Shape memory polymer 115 is a polymer that experiences a high degree of shape memory effect. Shape memory polymer 115 can be an acrylate-based network polymer or any other non-toxic polymer with a large shape memory effect and a glass (or phase) transition temperature below that of human body temperature and above that of room temperature. When shape memory polymer 115 is at a temperature below its glass (or phase) transition temperature, it is in a reduced-free volume glassy state that restricts micro-Brownian motion but still exhibits nonequilibrium chain motion over extended time scales. When shape memory polymer 115 is heated to a temperature above its glass (or phase) transition temperature, the polymer chains of shape memory polymer 115 are allowed to move and be deformed more freely as a series of relaxation processes take place. Shape memory polymer 115 may be easily folded when its temperature is above its glass (or phase) transition temperature and will retain this folded shape when cooled below its glass (or phase) transition temperature. When raised above its glass (or phase) transition temperature, shape memory polymer 115 will return to its unfolded shape without the application of any external forces.

The shape transition of shape memory polymer 115 may also be accomplished by various other external stimuli including light, humidity, electric fields, or magnetic fields. In other embodiments, shape memory polymer 115 may be formed through radical photopolymerization of tert-butyl acrylate and poly-(ethylene glycol) dimethacrylate to yield SMP networks. The crosslinking density and corresponding physical properties of shape memory polymer 115 may be altered during radical photopolymerization by changing the weight percent of crosslinking monomers in solution.

In the embodiments illustrated in FIG. 1, electrode heads 120 can be at least partially embedded into elastomer body 110. Electrode heads 120 may be configured to adhere to elastomer body 110 by double sided adhesive 145 and further secured by additional elastomer. In some embodiments, electrode heads 120 can be adhered to convex bumps 130 of elastomer body 110 and may be positioned on the neutral mechanical plane of elastomer body 110. Electrode heads 120 may be made from silver electroplated copper or any another conductive metal such as aluminum or annealed copper and electroplated with any sufficiently conductive metal such as gold or platinum or any alloy thereof. In other embodiments, electrode heads 120 may not be electroplated and may be made entirely from an electrically conductive metal such as silver, gold, platinum, aluminum or copper.

Electrode heads 120, in accordance with some embodiments, can be passive electrodes and deliver no electrical stimuli to a user and only detect brainwave when in contact with the skin of the ear canal of the user. Electrode heads 120 may not need electrically conductive gel to detect the brainwave signals of a user and the brainwaves may include EEG signals, EOG signals, or EMG signals, or any other bioelectrical signals. In still further embodiments, electrode heads 120 have a low electrode-skin contact impedance. The electrode-skin contact impedance may be as low as 10,000 Ohms (10 kΩ). Electrode heads 120 may be readily deoxidized by a solution of vinegar and salt or any other solution capable or removing oxide buildup from the surface of a metal. Furthermore, the number electrodes adhered to elastomer body 110 is not limited.

In some embodiments, electrode heads 120 may be directly connected to electrode tails 125. In some embodiments, electrode tails 125 can be fully embedded into elastomer body 110 such that they are not exposed. In certain embodiments, electrode tails 125 can be made from the same material as electrode heads 120. Electrode tails 125 may be silver electroplated copper wires or any other electrically conductive metal or metal alloy. In other embodiments, electrode tails 125 are made from a single type of metal such as copper or silver and may not be electroplated or may be made from a metal alloy such as a gold/silver alloy or a copper/silver alloy.

Electrode tails 125 can be attached to external wires 140 through the use of electrically conductive epoxy 135. External wires 140 may be medical grade silver wires and well insulated. In some embodiments, electrically conductive epoxy 135 is a silver epoxy or may contain any other electrically conductive metal such as copper or gold. Electrically conductive epoxy 135 can be fully embedded into elastomer body 110. External wires 140 may further connect to a wireless device to transmit detected brainwave signals to a computer or may be directly connected to a computer such as an OpenBCI© board where the detected brainwave signals can be interpreted.

Figure 2A:
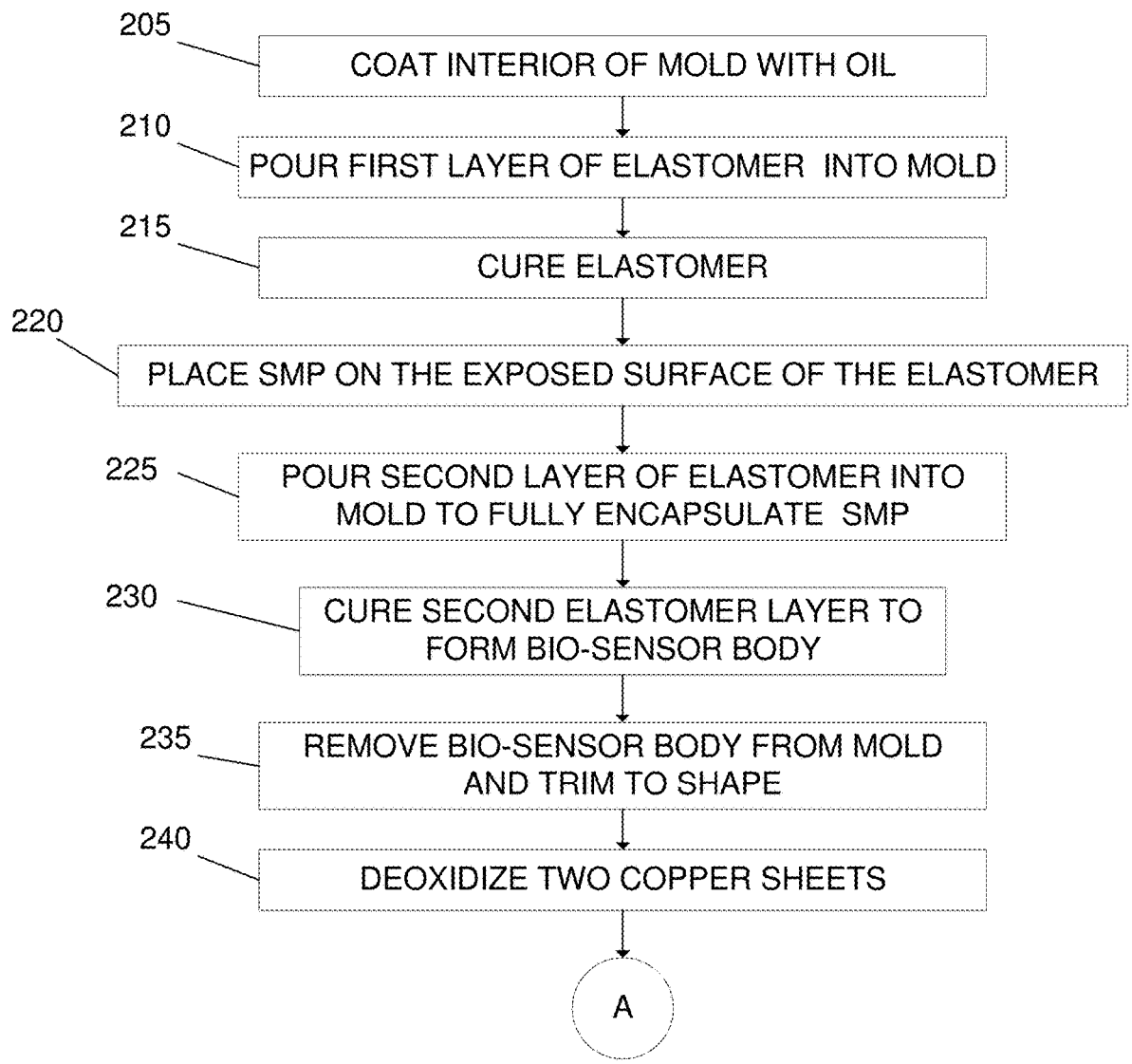
FIGS. 2A and 2B are flowcharts illustrating an example of a set of operations for the production of an in-ear biosensor in accordance with some embodiments of the present technology.
Figure 2B:
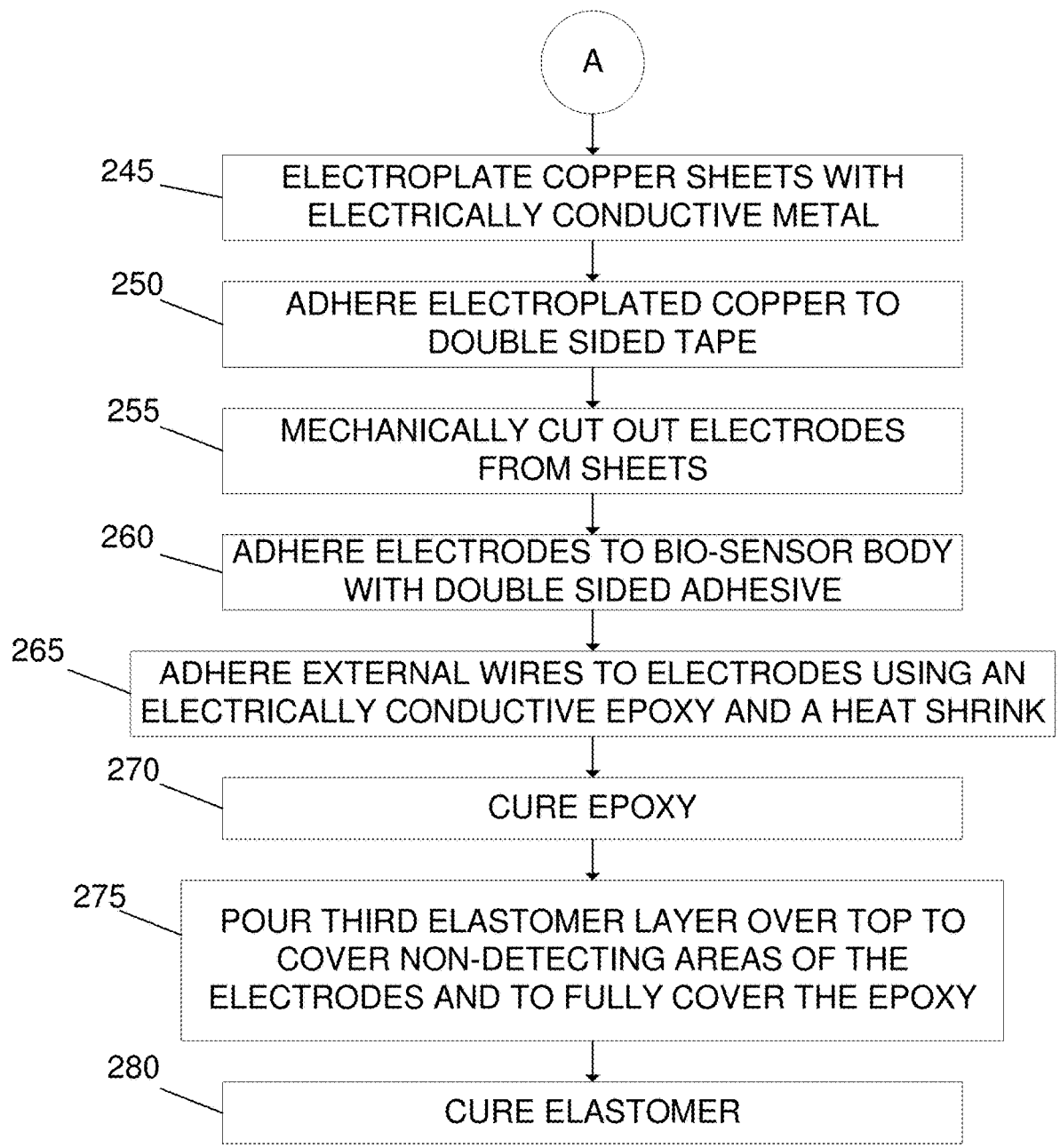

FIGS. 2A and 2B are flowcharts illustrating an example of a set of operations for the production of an in-ear biosensor in accordance with some embodiments of the present technology. In process step 205, a layer of oil can be applied to the interior a mold where the biosensor is to be formed. In some embodiments, the oil may be a vegetable oil, an animal oil, or a petroleum oil, or any other oil capable of preventing the elastomer from adhering to the mold. In process step 210, a first layer of elastomer can be poured into the mold. In some embodiments, the bottom surface of the mold contains surface features to form convex humps onto the surface of the elastomer.

In process step 215, the elastomer can be cured. In accordance with some embodiments, the curing of the elastomer can involve the formation of crosslinks between the polymer chains of the elastomer to fully solidify the elastomer. The crosslinking may be achieved through heat treatment, ultraviolet light (UV) activation, or by the addition of crosslinking agent specific to the elastomer or by any other method that results in the crosslinking of the elastomer. In process step 220, a piece of shape memory polymer can be placed into the mold and onto the surface of the cured elastomer. The shape memory polymer may be rectangular, square, or circular or any other shape as to provide internal structure to the biosensor.

In process step 225, a second layer of elastomer can be poured into the mold to fully encapsulate the shape memory polymer. The second layer of elastomer can be of similar thickness to the first layer of elastomer. In process step 230, the second layer of elastomer can be cured. The curing of the second elastomer layer forms a single, continuous, molecularly bonded connection between the first and second elastomer layers such that they become a single elastomer thereby forming the body of the biosensor. The curing of the second elastomer layer may be done by heat treatment, UV activation, or by the addition of a crosslinking agent specific to the elastomer. The method of curing the first elastomer layer and the second elastomer layer may or may not be the same method. In process step 235, the now formed biosensor body can be removed from the mold is trimmed to a desired shape. In some embodiments, the biosensor body when removed from the mold will have a flat side and a side with convex humps on its surface.

In process step 240, copper sheets can be deoxidized and cleaned. In some embodiments, the copper sheets may be as thin as 25 micrometers and may be deoxidized by the application of a salt and vinegar solution, a deoxidizing agent, or by any other method to sufficiently remove an oxide layer that may have formed on the surface of the copper. In process step 245, the copper sheets can be electroplated with an electrically conductive metal. The electroplating agent may be any electrically conductive metal such as silver, gold, platinum, or any other metal or mixture of metals. In process step 250, the copper sheets are adhered to a double-sided adhesive. In some embodiments, the double-sided adhesive may be a double-sided tape or a heat resistant glue. Following the addition of the double-sided adhesive, in process step 255 the copper sheets are mechanically cut into the shape of electrodes. The mechanical cutter can be operated manually or may be controlled by a robotic or computational device. In process step 260, the electrodes can be adhered to the biosensor body by using the exposed side of the double-sided adhesive. In certain embodiments, the electrodes can be adhered to the convex humps on the surface of the biosensor body.

Still referring to FIG. 2, in process step 265, external wires can be attached to the non-detecting ends of the electrodes through the use of an electrically conductive epoxy and secured in place with heat shrinking tubes. The electrically conductive epoxy may contain silver or any other electrically conductive metal such as gold, platinum, copper, annealed copper, or aluminum. In some embodiments, the external wires may be well insulated silver wires, well insulated copper wires, well insulated gold wires, or any other type of well insulated electrically conductive wire. In process step 270, the electrically conductive epoxy can be cured until the epoxy fully hardens and may be cured by heat treatment, air-exposure, or any other method to harden the epoxy.

In process step 275, a third layer of elastomer can be poured on top to cover the non-detecting ends of the electrodes as well as the electrically conductive epoxy. In process step 280, the third layer of elastomer can be cured by heat treatment, UV activation, or by the addition of a crosslinking agent, or by any other method of curing. The method of curing the third elastomer layer may or may not be the same method used to cure either the first or second elastomer layer. When cured, the third elastomer layer fully integrates into the biosensor body by chemically bonding to the surface. Each layer of elastomer may be chemically identical or chemically distinct. The elastomer layers may be composed of polydimethylsiloxane or any other non-toxic soft polymer.

Figure 3:
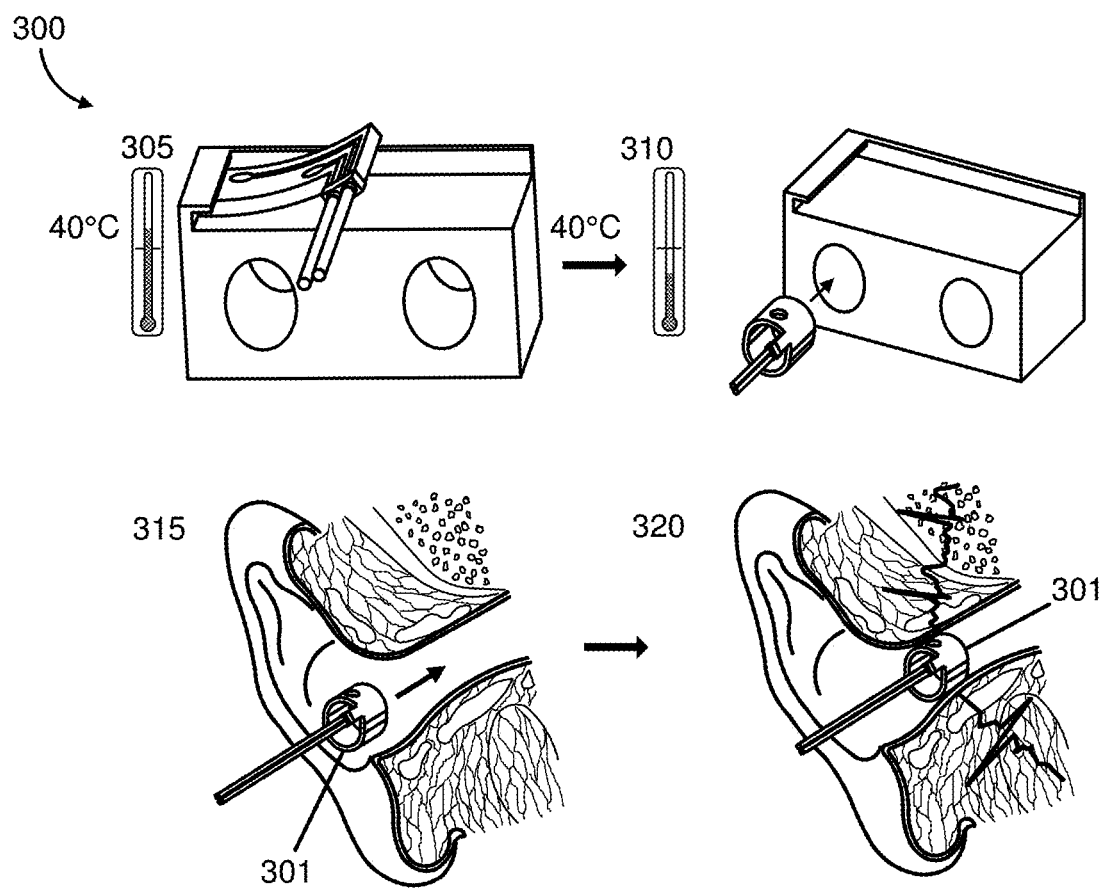
FIG. 3 illustrates the operation of an in-ear biosensor in which some of the embodiments of the present technology may be utilized.

FIG. 3 illustrates the operation of an in-ear biosensor in which some of the embodiments of the present technology may be utilized. In step 305, a heated biosensor can be rolled into a hollow cylindrical shape through the use of a mold. In some embodiments, the biosensor can be folded or otherwise deformed (instead of rolled) to create a shape that could fit into the ear canal (e.g., earpiece 301). The mold contains a lip to facilitate the folding of the biosensor and a cylindrical tube to hold the molded biosensor in place. At the elevated temperature, the shape memory polymer contained within the biosensor is at a temperature above its glass (or phase) transition temperature. In this state, the shape memory polymer is readily deformable into a hollow cylindrical shape.

In step 310, the rolled (or folded) biosensor can be inserted into the cylindrical mold and allowed to cool to room temperature. When the biosensor cools to room temperature, the temperature of the shape memory polymer falls below the glass (or phase) transition temperature of the shape memory polymer. The shape memory polymer transitions to a glassy state when below the glass (or phase) transition temperature which allows the biosensor to maintain a hollow cylindrical shape. In step 315, the cooled biosensor can be inserted into the ear canal of a user where it is warmed by the body heat of the user.

In step 320, body heat causes the shape memory polymer in the biosensor to relax once inside the ear, allowing the polydimethylsiloxane to recover and apply pressure to the walls of the inner ear, thus maximizing the contact of the electrodes with the ear walls for a better-quality signal. The partially unrolled biosensor does not block the ear canal of the user. In some embodiments, the partially unrolled biosensor when inserted into the ear canal of a user allows the user to continue to hear sound and further allows for fluid transfer to take place within the ear.

In some embodiments, the electrodes can be positioned to make contact with the top and bottom of the ear canal thereby creating an electric dipole to enhance the detection of brainwaves. In other embodiments, the biosensor makes no use of electrically conductive gel to facilitate the detection of brainwaves. The biosensor records via the set of electrodes and transmits brainwaves via the external wires attached to the electrodes where the information recorded by the electrodes is transmitted to an external apparatus such as an OpenBCI© board for interpretation. The electrodes do not provide any energy, transmissions or electrical signals to the user.

Figure 4:
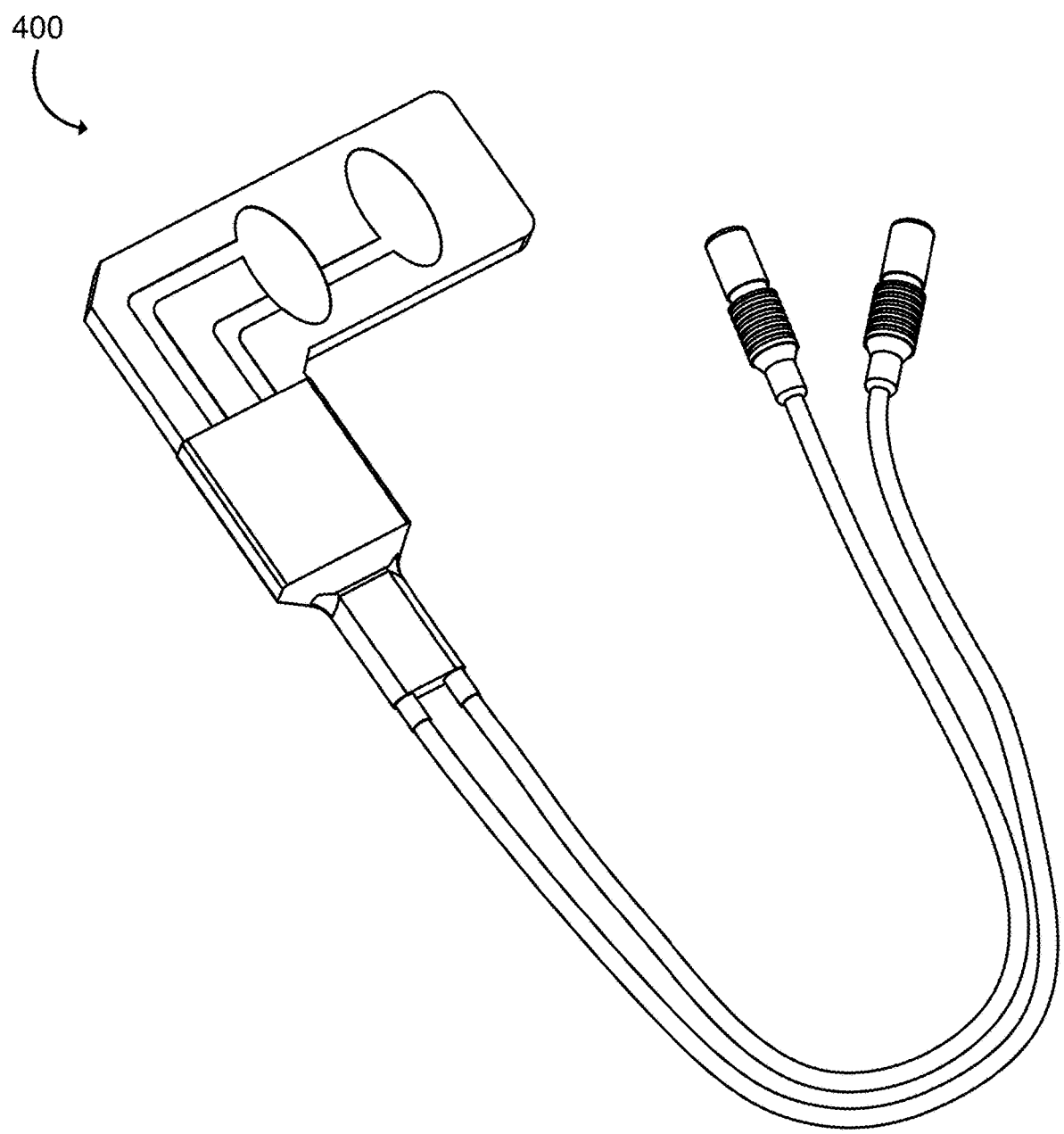
FIG. 4 illustrates an example of a polysomnography sensor in which some embodiments of the present technology may be utilized.

FIG. 4 illustrates an example of a polysomnography sensor 400 in which some embodiments of the present technology may be utilized. In the embodiments illustrated in FIG. 4, the PSG sensor 400 includes a set of electrodes connected to a set of external wires through an electrically conductive epoxy and a heat shrinking tube. The electrodes are partially embedded into the body of the PSG sensor where the non-sensing electrode elements are fully embedded into the PSG sensor while the sensing elements of the electrode are exposed. In some embodiments the electrodes are made of silver electroplated copper. In other embodiments, the copper electrodes may be electroplated with gold, platinum, aluminum, an electrically conductive metal alloy, or any other metal or alloy. In still further embodiments, the electrodes may not be electroplated and may instead be made from a single metal or metal alloy such as a silver or a gold/silver alloy, or a silver/copper alloy. In these embodiments, the electrically conductive epoxy may include silver, copper, gold, platinum, or another metal or alloy or any combination thereof.

The external wires may be heavily insulated to prevent any signal interference and may be medical grade silver wire, medical grade copper wire, or medical grade gold wire. When in contact with the skin of the ear canal, the electrodes can detect the brainwaves of a user with impedance values as low as 10 kΩ. Furthermore, the electrodes can detect the brainwaves of a user by making direct contact to the skin of a user without the use of any other substance and do not provide any type of energy or simulation to the user.

The external wires of the of the PSG sensor 400 can be connected to an OpenBCI Board© or any other device capable of interpreting bio-signals and are well-insulated and of a length similar to that of normal in-ear headphones to ensure a safe distance between the board and the user's face. The external wires may further connect to a Bluetooth device to transmit the recorded bio-signals wirelessly. The information recorded by the electrodes and transmitted by the external wires can be compatible with a wide range of software programs that are capable of interpreting bio-information such as EEG signals, EOG signals, or EMG signals, or any other relevant bio-signal.

In some embodiments, the body of the PSG sensor 400 can be rectangular and made from a soft, non-toxic elastomer. In some embodiments, the elastomer can be a polydimethylsiloxane elastomer, a chemical derivative of polydimethylsiloxane, or any other similar elastomer with a crosslinking density as to ensure flexibility and rigidity. The elastomer body may contain one or more convex surface features located on one or more sides of the elastomer body. In some embodiments, the convex surface features may act as a hinging mechanism when the PSG sensor 400 can be curled into a hollow cylindrical shape allowing for insertion within an ear canal. The elastomer body of the PSG sensor 500 can fully encase a shape memory polymer. The shape memory polymer may be rectangular in some embodiments and run down the central axis of the PSG sensor 400. In other embodiments, the PSG sensor 400 and the shape memory polymer may be square, circular, hexagonal, elliptical or shaped in any other way.

The shape memory polymer may have a glass (or phase) transition temperature below the surface temperature of an ear canal and above a room temperature. In some embodiments, the shape memory polymer may contain a fixed state that it conforms to when its temperature is higher than its glass (or phase) transition temperature and may further contain a programmed state which it conforms to when folded and cooled below its glass (or phase) transition temperature. The shape memory polymer may transition without the application of any external forces from a programmed state to a fixed state when its temperature is raised above its glass (or phase) transition temperature. The transition from a programmed state to a fixed state may also be accomplished by stimuli including temperature, light, humidity, electric fields or magnetic fields. In still further embodiments, the shape memory polymer may be an acrylate-based network polymer formed through the radical photopolymerization of tert-butyl acrylate and poly-(ethylene glycol) dimethacrylate.

Figure 5:
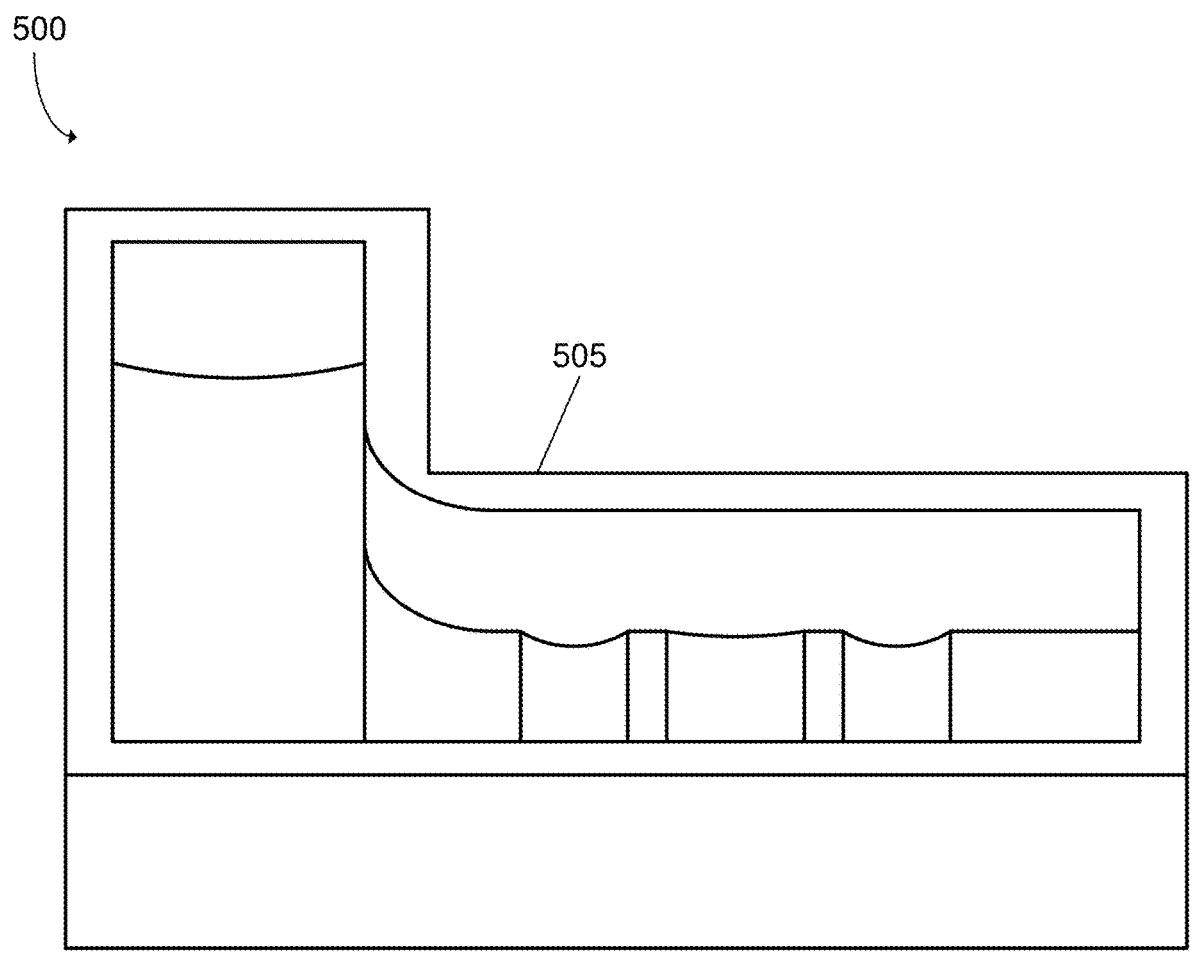
FIG. 5 illustrates an example a mold that may be used in the production of an in-ear biosensor according to one or more embodiments of the present technology.

FIG. 5 illustrates an example a mold 505 that may be used in the production of an in-ear biosensor in one or more embodiments of the present technology. In the embodiments illustrated in FIG. 5, mold 505 is three dimensional and contains concave surface features at its base such that an object molded by the mold would obtain convex surface features. In some embodiments, mold 505 can be three-dimensionally (3D) printed. Mold 505 may be made from polylactic acid or acrylonitrile butadiene styrene or any other plastic compatible with 3D printing. In other embodiments, mold 505 may be made from metals such as iron, steel, aluminum or any other similar metal or an alloy thereof. Mold 505 can be resistant to heat treatment and not corrode in the presence of oils including cooking oil, animal oil, vegetable oil, or petroleum oil.

Figure 6:
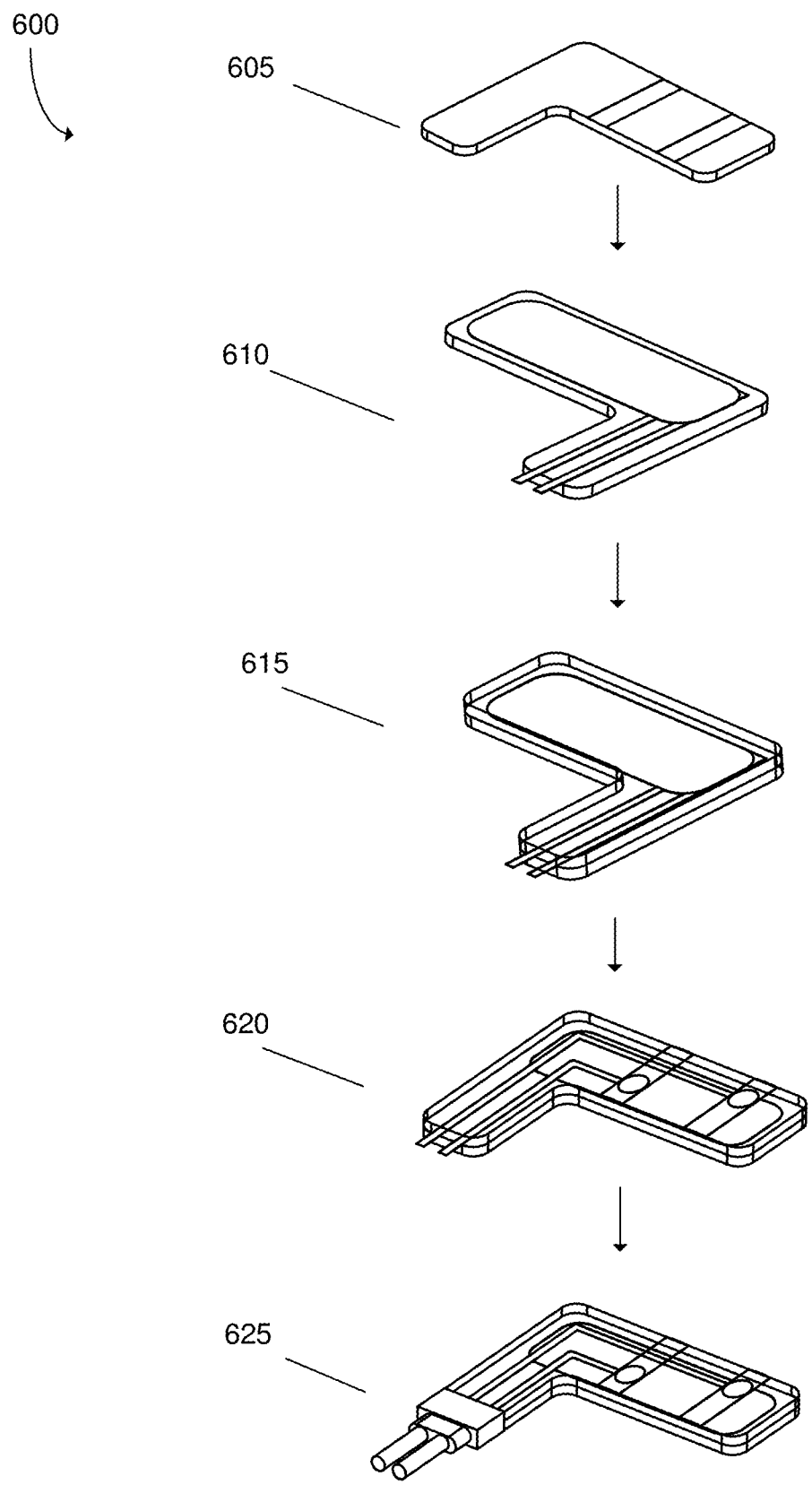
FIG. 6 illustrates a manufacturing process for an in-ear biosensor in accordance with some embodiments of the present technology.

FIG. 6 illustrates an example of a manufacturing process 600 for an in-ear biosensor in accordance with some embodiments of the present technology. As illustrated in FIG. 6, in step 605, a polydimethylsiloxane layer can be cast with convex domes on one side using 3D-printed mold and allowed to cure in the mold. In step 610, once the bottom polydimethylsiloxane layer is cured, a shape memory polymer can be placed on top of its flat side such that the convex domes imprinted by the 3d-printed molded remain unobstructed.

In step 615, another flat layer of polydimethylsiloxane can be poured atop the shape memory polymer and allowed to cure within the mold. The added layer of polydimethylsiloxane is poured such that it fully covers the shape memory polymer and bonds to the first layer of polydimethylsiloxane during curing. In step 620, silver-electroplate copper electrodes can be adhered to the top of the earpiece using a double-sided adhesive and non-sensing components of the electrodes are covered with another layer of polydimethylsiloxane. In step 625, protected silver wires can be connected to the electrodes with silver epoxy and covered with heat-shrinking tubes. The silver epoxy can be allowed to cure and an additional layer of polydimethylsiloxane can be added to cover the silver epoxy and is then allowed to cure. Once the final layer of polydimethylsiloxane has cured, the in-ear biosensor is ready for use.

Figure 7:
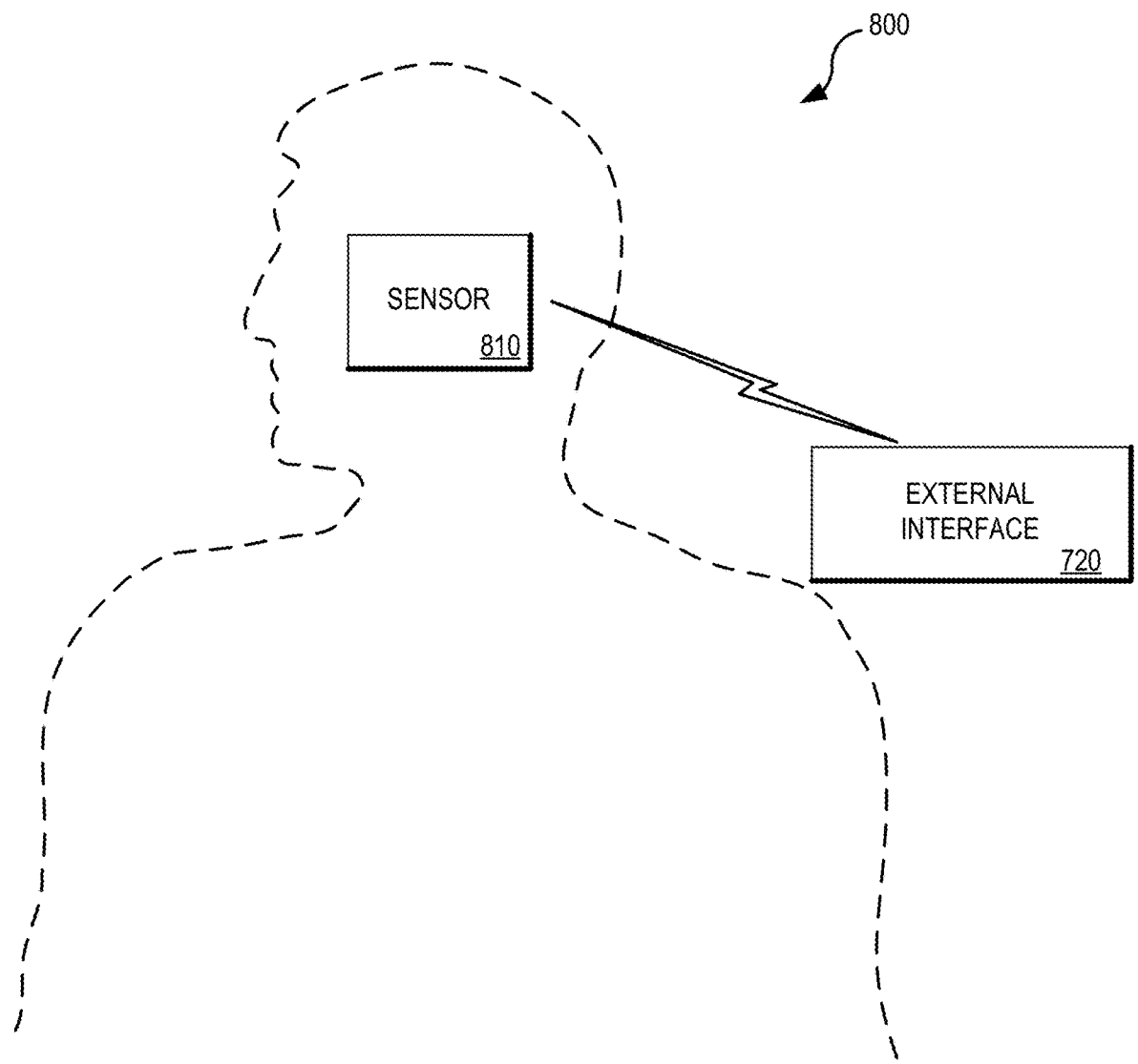
FIG. 7 illustrates an example of a biosensor connecting to an external interface in accordance with various embodiments of the present technology.

FIG. 7 illustrates an example of a biosensor 710 connecting to an external computing device 720 in accordance with various embodiments of the present technology. Biosensor 710 can be designed to create an in-ear PSG to provide fine-tuned sleep quality monitoring that can be classified to appropriate sleep stages automatically using external computing device 720. The system illustrated in FIG. 7 can allow for the collection of recordings related to human bioelectrical signals involving EEG, EOG, and EMG using various embodiments of a less invasive wearable biosensor 710 for this special purpose during sleep. The biosensor 710 or earpiece aims to be convenient and comfortable for long term use and reliability. The advantages of the design of this product include an unobtrusive and easy-to-use bio-system for human sleep stage classification using a non-invasive technique for brain-computer interaction. Additionally, there is no need for sticky and uncomfortable conductive gels that dry out and thus have diminished performance over time. Various embodiments allow for the wearable sleep devices for automatically assessing and scoring sleep quality and staging in outpatient and home settings.

Fast frequency low amplitude waves, such as the 40 Hz frequency signal, can be challenging to distinguish from the background. Various embodiments can detect fast eye movements, chewing, K-complexes and delta waves and accurately assign sleep stages in REM, delta sleep and stage N2 once. This allows high accuracy of stage detection during sleep, comparable to that of the traditional polysomnogram.

In some embodiments, computing device 720 may be configured to provide feedback and recommendations for a variety of applications. For example, in some embodiments, computing device may analyze brainwaves and provide feedback for sleep improvement. This may not just be for people with sleep disorders, but anyone can get a full night EEG/EOG/EMG sleep analysis by wearing the in-ear biosensor as they sleep. Various embodiments of the present technology can detect the raw EEG signals and communicate them to a transponder, which can then filter and analyze the data using machine learning. Metrics such as sleep stages, jaw movement, and eye movement can make the user aware of any abnormalities and provide them with information about their sleep quality in general.

In some embodiments, computing device 720 can be used for epilepsy onset detection. For example, people with certain types of epilepsy that have recognizable EEG waveform markers can be alerted to a seizure before it actually occurs. They could wear the in-ear biosensor as they sleep/drive/work/etc., and the device could warn their cell phone or caretaker right before a seizure. In some embodiments, the system could even be connected via software to a patch that releases medication to the user as soon as the onset of the seizure is detected.

Another application is autism onset detection. Like the epilepsy patient, someone with autism can wear the biosensor and be alerted of abnormal brain activity before an episode occurs. Children suspected of being autistic can also be diagnosed using the in-ear biosensor for abnormal brain function.

Some embodiments can be used for ADHD detection. For example, the in-ear biosensor can be used to analyze the passive or active focus state of its wearer, and can be employed to either diagnose or treat ADHD patients by analyzing how they respond to stimuli.

Some embodiments may be used as a smoke quitting assistant. Various embodiments of the software running on computing device 720 can work with the in-ear biosensor and can be trained to recognize symptoms of nicotine withdrawal of the wearer. This data can be used to diagnose smoking habits, and even interface with nicotine patches to help the wearer quit smoking.

Another application is meditation enhancement. In some embodiments, the in-ear biosensor can detect frequency shifts in brain activity and can be used to detect the low frequency peaks that are associated with meditating. The biosensor and its software can be used to give the user feedback on their meditation practices, as well as directly interact with the user to help train them by changing the music/lights and/or providing personalized goals and challenges.

Some embodiments may use the biosensor and computing device as a driving drowsiness and distraction prevention technology. As with ADHD detection, the in-ear biosensor can be used to analyze the passive or active focus state of the user while driving. This information can be used to help keep the driver awake and aware, perhaps by interfacing with the phone to sound an alarm or vibrate.

Figure 8A:
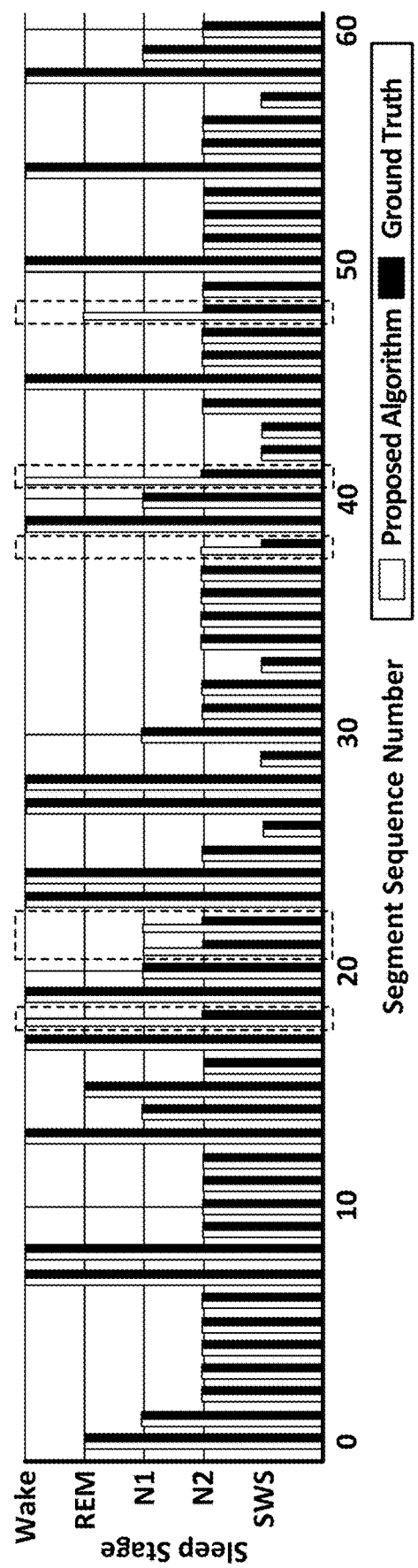
FIG. 8A illustrates an example of a hypnogram of 30-minute data resulted by the proposed system.
Figure 8B:
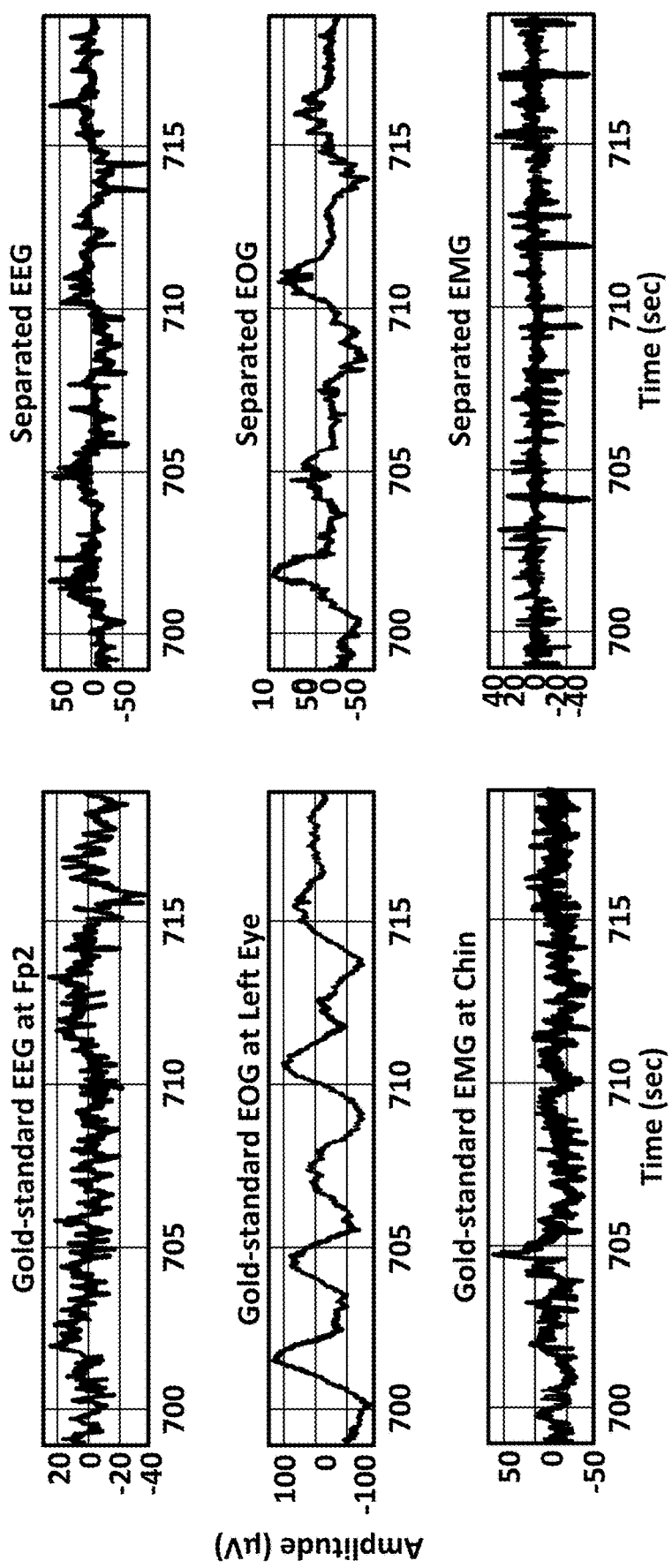
FIG. 8B illustrates a comparison of EEG, EOG, and EMG signals recorded by the gold-standard device and extracted by our signal separation algorithm using the single-channel in-ear signal during stage N1 of a real sleep study.
Figure 8C:
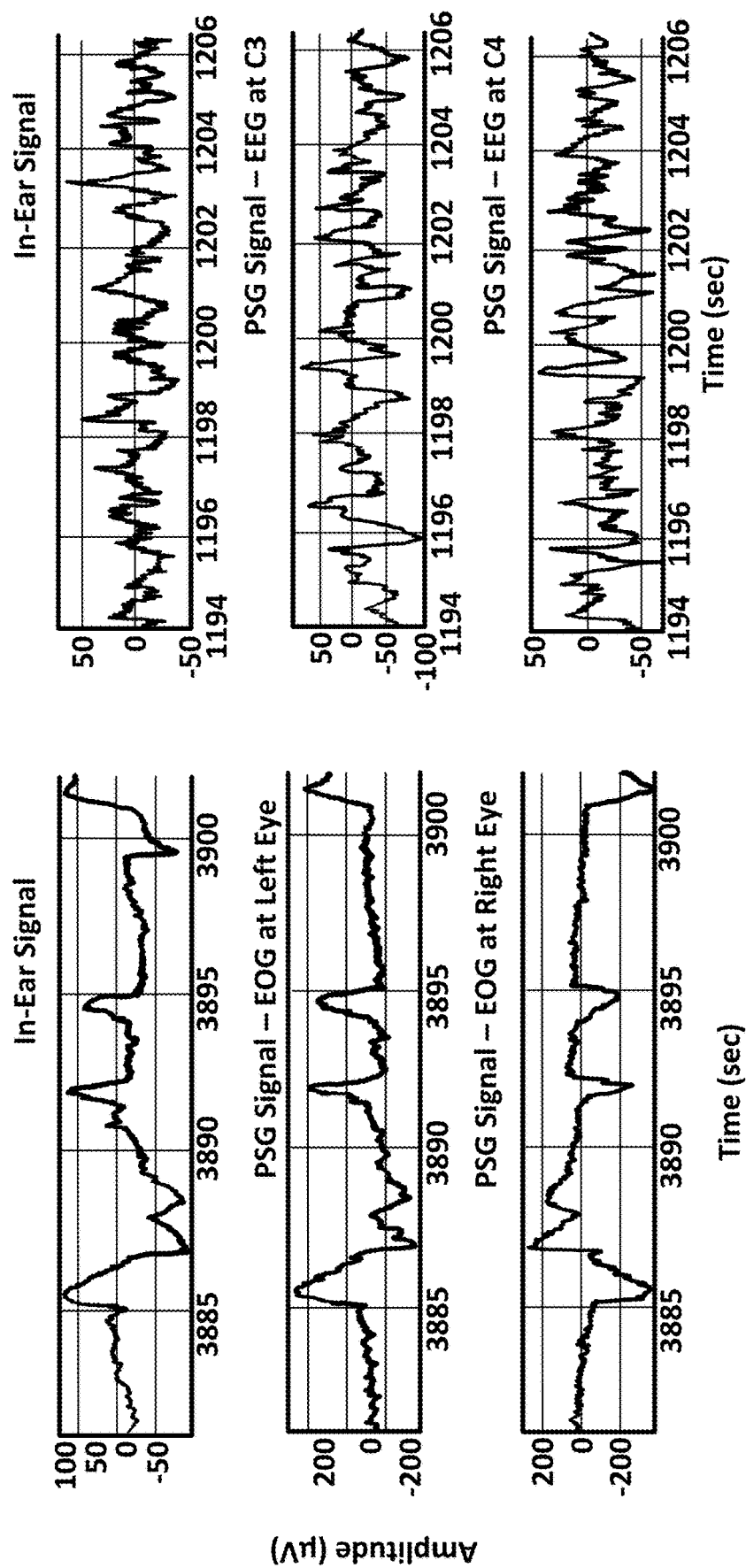
FIG. 8C illustrates a comparisons of standard PSG with In-ear PSG measurements of rapid eyes movements in REM sleep (left fig.) and delta waves in N3 sleep (right fig.).

FIGS. 8A-8C visually demonstrates results of a sleep staging model using the EEG, EOG, and EMG provided by some embodiments of an in-ear PSG biosensor. Compared to the ground truth, various embodiments of the end-to-end system can achieve 94% accuracy in sleep stage classification on average when using the three separated signals as input. Some embodiments may use a signal separation algorithm to determine the quality of EEG, EOG, and EMG signals extracted from the in-ear signal. FIGS. 8A-8C demonstrate all three types of signals achieved in stage N1 of a real sleep study in two distinct ways. As shown, various embodiments of the signal separation algorithm are capable of separating EEG, EOG, and EMG signals with high quality and similar shape compared to the corresponding signals captured by the gold-standard device. There are tested cases in which the signals were separated nicely, and such separated signal can be used for sleep staging.

Various embodiments of the in-lab sleep studies last for approximately four hours per subject, during which time subjects will be informed about the procedure, potential risks, and expectations by a study physician or other proctor. The subjects can be asked to carefully look over and sign the consent form and will be informed that they can terminate the experiment at any time. If they consent to participating, they will be outfitted with 10 PSG electrodes on their head and face using conductive gel and gauze to hold them in place. Once the PSG electrodes are in place, the study physician or proctor will insert the rolled In-Ear Biosensors into the subject's outer ear canal, ensuring their comfort in the process.

Various bio-signals, including EEG, EMG, and EOG, will be tested for veracity by showing visual stimuli to the subject on a computer screen. The participant will then attempt to sleep in a sanitized bed in the lab for approximately two and a half hours. They will then have all the electrodes and in-ear sensors removed and be asked a few questions about comfort and the experience of wearing the in-ear sensors. After completing the session, participants will be recompensed for their time.

Data acquired by the In-Ear PSG device is analyzed in three steps using statistical software. First, the digital in-ear signal is preprocessed through different band-pass filters to eliminate possible noises (e.g. electric noise at 60 Hz, etc.). In the second step, the preprocessed signal is separated into individual signals of interest (i.e. EEG, EOG, and EMG) through an adaptive separation method, which is developed based on a non-negative Matrix Factorization algorithm, due to the constraint on electrode placement. Finally, visual comparisons between both the original in-ear signal and the three separated signals captured by a gold standard PSG are made by a certified sleep technician. By analyzing the in-ear signal in this way, various embodiments can evaluate the interpretability of the In-Ear PSG through its recorded original signal as well as test the possibility of separation of bioelectrical signals generated by the human brain, eyes, and muscles of the outer ear that are mixed in the in-ear signal. Using the algorithm, some embodiments can quantify the accuracy as a percentage of the traditional polysomnogram signal.

FIG. 8A illustrates an example of a hypnogram of 30-minute data resulted by the proposed system. In this figure, the sleep staging done for 60 segments (i.e. each 30-second period) using various embodiments of a sleep stage classification algorithm is compared with the ground truth. The misclassification of the algorithm is marked by dashed rectangles. FIG. 8B illustrates a comparison of EEG, EOG, and EMG signals recorded by the gold-standard device and extracted by our signal separation algorithm using the single-channel in-ear signal during stage N1 of a real sleep study. FIG. 8C illustrates a comparisons of standard PSG with In-ear PSG measurements of rapid eyes movements in REM sleep (left fig.) and delta waves in N3 sleep (right fig.). This demonstrates the ability to determine eye and brain waves from a mixed in-ear signal.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein,"

"above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology may be recited as a system claim, other aspects may likewise be embodied as a system claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A biosensor for detecting physiological signals, the biosensor comprising:
    an earpiece formed of a material comprising at least one of: a shape memory material and a temperature-dependent phase transition material;
        wherein the earpiece comprises a folded state produced by folding the material when heated above a glass transition temperature of the material and maintains the folded state when cooled to below the glass transition temperature of the material, and
        wherein, when inserted into an ear canal of a user, the material of the earpiece in the folded state is heated by the ear canal above the glass transition temperature of the material and partially unfolds to conform with a shape of the ear canal;
    a set of flexible conductive electrodes located on an outer surface of the earpiece;
    a set of wires electrically connected to the set of flexible conductive electrodes; and
    an elastomer overlaid onto the set of flexible conductive electrodes.

2. The biosensor of claim 1, wherein the glass transition temperature of the material is less than, or slightly above, a body temperature of the user and greater than a room temperature.

3. The biosensor of claim 2, wherein the glass transition temperature of the material is between about 20° C. and about 50° C.

4. The biosensor of claim 1, wherein the set of flexible conductive electrodes measure one of the following: temperature, heart rate, acceleration blood pressure, electroencephalography (EEG) signals, electrooculography (EOG) signals, and electromyography (EMG) signals, and electrocardiogram (EKG or ECG) signals.

5. The biosensor of claim 1, wherein the set of flexible conductive electrodes includes electrodes formed of at least one of: copper, gold, silver, platinum, titanium, graphite, graphene, nanotubes, nanowires, polymers, nanoparticles, polymer composites, microparticle composites, and nanoparticle composites.

6. The biosensor of claim 1, wherein the set of wires is connected to a wireless transmitter configured to wirelessly transmit collected signals to a data connection system.

7. The biosensor of claim 1, wherein the material is at least one of: encapsulated inside of the elastomer and bonded to one side of the elastomer.

8. A system comprising:
    a biosensor configured to: securely fit within an ear canal of a user and collect brainwave data, the biosensor comprising:
        an earpiece formed of a material comprising at least one of: a shape memory material, and a temperature-dependent phase transition material,
            wherein the material is at least one of: encapsulated inside of an elastomer, and attached to one side of the elastomer,
            wherein the earpiece comprises a folded state produced by folding the material when heated above at least one of: a glass transition temperature and a phase transition temperature of the material and maintains the folded state when cooled to below the at least one of: the glass transition temperature and the phase transition temperature of the material, and wherein, when inserted into the ear canal of the user, the material of the earpiece in the folded state is:
heated by the ear canal above at least one of: the glass transition temperature and the phase transition temperature of the material; and
partially unfolds to conform with a shape of the ear canal of the user;

a set of flexible conductive electrodes located on an outer surface of the earpiece;

a set of wires electrically connected to the set of flexible conductive electrodes; and an elastomer overlaid onto the set of flexible conductive electrodes.

9. The system of claim 8, wherein the material has: a programmed state and a fixed state.

10. The system of claim 9, wherein the material of the earpiece transitions from the programmed state to the fixed state when a temperature of the material is raised to a temperature of from about 30° C. to about 50° C.

11. The system of claim 8, wherein at least one of: the glass transition temperature and the phase transition temperature of the material is: less than or above a body temperature of the user and greater than room temperature.

12. The system of claim 8, wherein:
when heated above at least one of: the glass transition temperature and the phase transition temperature of the material and folded, the earpiece assumes a hollow cylindrical shape; and
when cooled below at least one of: the glass transition temperature and the phase transition temperature of the material, the earpiece maintains the hollow cylindrical shape.

13. The system of claim 12, wherein the earpiece in, the hollow cylindrical shape is small enough to be inserted into the ear canal of the user.

14. The system of claim 13, wherein, when inserted into the ear canal of the user, the material of the earpiece is heated by the ear canal of the user to a temperature of from about 30° C. to about 50° C. and partially unfolds to conform with the shape of the ear canal of the user.

15. The system of claim 14, wherein the earpiece, once partially unfolded, creates a low impedance electrical connection between the set of flexible conductive electrodes and a surface of the ear canal of the user.

16. The system of claim 8, wherein the set of flexible conductive electrodes comprises: ultra-thin silver electroplated copper and a silver epoxy.

17. The system of claim 8, wherein the elastomer comprises at least one of: polydimethylsiloxane, ecoflex, and dragon skin.

* * * * *